(12) United States Patent
Linderman

(10) Patent No.: US 9,192,335 B2
(45) Date of Patent: Nov. 24, 2015

(54) ATHLETIC GLOVE PROVIDING FEEDBACK REGARDING GRIP TO A WEARER

(71) Applicant: Michael Linderman, Ogdensburg, NY (US)

(72) Inventor: Michael Linderman, Ogdensburg, NY (US)

( * ) Notice: Subject to any disclaimer, the term of this patent is extended or adjusted under 35 U.S.C. 154(b) by 138 days.

(21) Appl. No.: 13/861,441

(22) Filed: Apr. 12, 2013

(65) Prior Publication Data

US 2014/0309547 A1    Oct. 16, 2014

(51) Int. Cl.
| | |
|---|---|
| *A61B 5/0488* | (2006.01) |
| *A63B 24/00* | (2006.01) |
| *A61B 5/00* | (2006.01) |
| *A61B 5/0492* | (2006.01) |
| *A61B 5/22* | (2006.01) |
| *G09B 19/00* | (2006.01) |

(52) U.S. Cl.
CPC .............. *A61B 5/6806* (2013.01); *A61B 5/0492* (2013.01); *A61B 5/225* (2013.01); *A61B 5/6825* (2013.01); *G09B 19/0038* (2013.01); *A61B 2505/09* (2013.01)

(58) Field of Classification Search
CPC .. A61B 5/0488; A61B 5/6806; A61B 5/0492; A61B 5/486; A61B 24/0062
USPC .......... 600/372, 382, 384, 386, 388, 393, 546, 600/587, 595; 128/905; 601/40; 482/44, 47, 482/49; 434/155; 73/865.4; 2/159, 160, 2/161.1–161.8

See application file for complete search history.

(56) References Cited

U.S. PATENT DOCUMENTS

| | | | | |
|---|---|---|---|---|
| 4,355,645 | A | * | 10/1982 | Mitani et al. ................... 600/590 |
| 5,368,042 | A | * | 11/1994 | O'Neal et al. ................ 600/546 |
| 5,592,401 | A | | 1/1997 | Kramer |
| 5,930,741 | A | | 7/1999 | Kramer |
| 6,148,280 | A | * | 11/2000 | Kramer .......................... 702/153 |
| 6,275,996 | B1 | * | 8/2001 | Redwood et al. .................. 2/160 |
| 7,602,301 | B1 | * | 10/2009 | Stirling et al. ............. 340/573.1 |
| 8,280,169 | B2 | | 10/2012 | Linderman |
| 8,280,503 | B2 | | 10/2012 | Linderman |

(Continued)

OTHER PUBLICATIONS

Glazebrook, et al. "Medial Epicondylitis an Electromyographic Analysis and an Investigation of Intervention Strategies." The American journal of sports medicine 22.5 (1994): 674-679. Retreived from <http://ajs.sagepub.com/content/22/5/674.full.pdf+html> on Dec. 2, 2014.*

(Continued)

*Primary Examiner* — Devin Henson
*Assistant Examiner* — David J McCrosky
(74) *Attorney, Agent, or Firm* — Michael D. Eisenberg

(57) ABSTRACT

A glove for recording and displaying the critical set of electromyography (EMG) signals representing consecutive hand movements. The glove is for measuring EMG signals in a hand, and includes a glove body, and/or a plurality of EMG electrodes disposed at predetermined locations on an inner surface of the glove body, configured to sense a magnitude of a plurality of EMG signals over a period of time, a data acquisition circuit coupled to the plurality of EMG electrodes, configured to receive at least one of the plurality of EMG signals and to generate an output proportional to the magnitude of the at least one of the plurality of EMG signals sensed by at least one of the plurality of EMG electrodes, and a user feedback module located on an external surface of the glove body for providing a representation of the output of the data acquisition circuit.

12 Claims, 13 Drawing Sheets

(56) References Cited

U.S. PATENT DOCUMENTS

| | | |
|---|---|---|
| 2009/0000010 A1 | 1/2009 | Sunder et al. |
| 2010/0106044 A1* | 4/2010 | Linderman .......... 600/546 |
| 2011/0009768 A1* | 1/2011 | Kosierkiewicz .......... 600/554 |
| 2011/0276153 A1* | 11/2011 | Selner .......... 700/91 |
| 2012/0172682 A1* | 7/2012 | Linderman et al. .......... 600/301 |
| 2014/0012157 A1* | 1/2014 | Gilhuly .......... 600/554 |
| 2014/0200432 A1* | 7/2014 | Banerji et al. .......... 600/383 |
| 2014/0309547 A1* | 10/2014 | Linderman .......... 600/546 |

OTHER PUBLICATIONS

Reference electrode. (n.d.) Mosby's Medical Dictionary, 8th edition. (2009). Retrieved from <http://medical-dictionary.thefreedictionary.com/reference+electrode> on Apr. 3, 2015.*

* cited by examiner

ATHLETIC GLOVE PROVIDING FEEDBACK REGARDING GRIP TO A WEARER

FIELD OF THE DISCLOSED TECHNOLOGY

The disclosed technology relates generally to athletic gloves and, more specifically, to athletic gloves including sensors for providing feedback to a wearer.

BACKGROUND OF THE DISCLOSED TECHNOLOGY

In many sports, such as golf, tennis, and baseball, the grip pressure applied by the athlete to the club, racket, or bat, is crucial to the player's accuracy and success. Thus, devices that provide athletes feedback regarding their grip are often considered useful for optimal game play.

Some existing athlete's gloves, such as SensoGlove® (at the time of this writing, for the following goods: sports or athletic glove, namely, glove used with swinging sporting equipment in the fields of baseball, hockey, tennis racquetball, and golf.) which is used for golfers, include pressure sensors located against the fingertips of the wearer of the glove. The pressure sensors include pressure transducers which output an electrical signal proportionate to the pressure applied by the user's fingers, and notify the user of the pressure used on a scale of 1-18. However, the measurements made by SensoGlove are based solely on the pressure applied by the user's fingers to the golf club, and do not take into consideration the physiological activity and/or tension in other muscles in the user's hand, which may have a great impact on the accuracy of play. Specifically, pressure sensor typically measure forces applied perpendicular to the sensor, and may overlook the effects of forces that are off-axis to the measuring surface, thereby providing information which is not sufficiently accurate for helping an athlete reach their optimal play ability. Additionally, the readings of a pressure sensor may be impacted by the length of the user's fingers, because longer fingers generate higher leverage forces and thus the leverage forces and the pressure applied may vary between different people, making it hard for a glove using pressure sensors to be suitable for different athletes.

Surface electromyography (EMG) is a method for recording bio-electrical signals of a muscle's activity by placing electrodes or other contact points on the skin adjacent the muscle. Existing EMG based devices for measuring grip pressure place the electrodes on the user's forearm and/or shoulder, and use the readings from muscles in these locations to determine the pressure applied to the item in the athlete's hands. However, placement of a device on the user's forearm or shoulder is likely to impede the user's range of motion, thus adversely affecting their ability to swing a golf club, baseball bat, or tennis racket.

Thus, there is a need for an EMG based device providing feedback to a user from the muscles of the hand, using electrodes. However, the challenge was where to place the electrodes/sensors on a hand in order to record the meaningful EMG signals during a series of very fast sequential hand movements.

SUMMARY OF THE DISCLOSED TECHNOLOGY

In one embodiment of the disclosed technology, a glove for measuring electromyography (EMG) signals in a hand is disclosed. In an embodiment, such a glove includes a glove body, a plurality of EMG electrodes, a data acquisition circuit coupled to the plurality of EMG electrodes, and a user feedback module. In an embodiment, the plurality of EMG electrodes are disposed at predetermined locations on an inner surface of the glove body, and configured to sense a magnitude of a plurality of EMG signals from a user's hand over a period of time. In an embodiment, the data acquisition circuit is configured to receive at least one of the plurality of EMG signals sensed by the EMG electrodes, and to generate an output proportional to the magnitude of the received EMG signal or signals. In an embodiment, the user feedback module comprises a display, on which a representation of the magnitude is visually presented to the wearer of the glove. In an embodiment, the user feedback module comprises a speaker, through which a representation of the magnitude is audibly provided to the wearer of the glove.

In an embodiment, the EMG electrodes are divided into pairs of EMG electrodes, each pair including an active electrode and a reference electrode, and the electrodes in each pair being coupled to two inputs of a differential amplifier. Such a coupling structure helps reduce the noise resulting from measurement of EMG signals on the palm and back side of a user's hand. In an embodiment, the active electrode is configured to sense EMG signals from a muscle of the hand, and the reference electrode is configured to be located above a bone of the hand or from the vicinity of a bone of the hand.

In an embodiment, when the glove is worn by a user, one pair of electrodes is placed such that the active electrode senses signals from a muscle group including the Opponens pollicis muscle and the Abductor pollicis brevis muscle and the passive electrode senses signals from the area of the radius bone. In an embodiment, when the glove is worn by a user, one pair of electrodes is placed such that the active electrode senses signals from the First dorsal interosseus muscle and the passive electrode senses signals from the dorsum area. In an embodiment, when the glove is worn by a user, one pair of electrodes is placed such that the active electrode senses signals from the Second dorsal interosseus muscle and the passive electrode senses signals from the dorsum area. In an embodiment, when the glove is worn by a user, one pair of electrodes is placed such that the active electrode senses signals from the Abductor digiti minimi brevis muscle and the passive electrode senses signals from the area of the ulnar bone.

In an embodiment, all the EMG electrodes are connected to a ground electrode, which may, for example, be placed around the wrist of a user wearing the glove. In an embodiment, at least one of the EMG electrodes comprises a flexible EMG electrode, which, in some embodiments, is as narrow (thickness) as 1 mm. In some embodiments, a flexible EMG electrode comprises a bulk material as well as conductive nano-particles and/or general purpose electrolyte particles. The flexible EMG electrodes may be connected to the glove body in any suitable manner. In some embodiments, the flexible EMG electrodes are adhered to the glove body using a suitable bonding material, such as an electrically conductive glue. In some embodiments, the flexible EMG electrodes are sewn onto the inner surface of the glove body. In some embodiments, the EMG electrodes are integrated into an inner surface of the glove body, thereby forming an intelligent glove for EMG recording. In some embodiments commercial of the shelf disposable or dry electrodes can be held in place by an elastic glove, e.g. golf glove or a rehabilitation glove.

In an embodiment, a user would wear gloves of the teachings herein as a pair, with right and left hand gloves. In an embodiment, the glove comprises an amplifier, which is connected to analog to digital converter, a wireless transmitter for transmitting EMG signals from the analog to digital converter to a remote computer or acquisition circuit. In some embodiment it is possible to send a signal to a remote computerized device using USB. In some embodiment it is possible record the EMG signal locally on a memory storage device.

A method for measuring electromyography (EMG) signals, in another embodiment of the disclosed technology, has the following steps. First, a plurality of EMG electrodes are placed at predetermined location on an inner surface of a glove body. The glove is then placed on the hand of a user, such that each of the EMG electrodes senses the magnitude of an EMG signal over time. The signals from the EMG electrodes are received by an acquisition circuit, and an output proportional to a magnitude of the received signals is then generated. Finally, a representation of the magnitude of the received signals is provided to the user, either visually, for example on a display.

The method may further have a step of coupling each pair of the plurality of electrodes to two inputs of a single differential amplifier, thereby defining an active electrode which is placed on the skin above a muscle, and a reference electrode which is placed above a bone. In an embodiment, one pair of electrodes is placed such that the active electrode senses signals from a muscle group including the Opponens pollicis muscle and the Abductor pollicis brevis muscle and the passive electrode senses signals from the area of the radius bone. In an embodiment, one pair of electrodes is placed such that the active electrode senses signals from the First dorsal interosseus muscle and the passive electrode senses signals from the dorsum area. In an embodiment, one pair of electrodes is placed such that the active electrode senses signals from the Second dorsal interosseus muscle and the passive electrode senses signals from the dorsum area. In an embodiment, one pair of electrodes is placed such that the active electrode senses signals from the Abductor digiti minimi brevis muscle and the passive electrode senses signals from the area of the ulnar bone.

In an embodiment, the method also comprises connecting all the EMG electrodes to a ground electrode, which may, for example, be placed around the wrist of a user wearing the glove. In an embodiment, placing the electrodes comprises placing at least one flexible EMG electrode, which, in some embodiments, is as narrow (thickness) as 1 mm. In an embodiment, the method comprises adhering the flexible EMG electrodes to the glove body using a suitable bonding material, such as electrically conductive glue. In an embodiment, the method may comprise sewing the flexible EMG electrodes are onto the inner surface of the glove body. In some embodiments, the method may comprise integrating the EMG electrodes into an inner surface of the glove body, thereby forming an intelligent glove for EMG recording. The integrating may include steps of contacting the electrodes with conductive glue, tempering, using a textile adhesive gluing the electrodes into the textile of the glove, tempering, soldering a signal wire to the electrode, encapsulating the soldering point with silicone, and finally tempering again. In another embodiment the method comprises first placing gel electrodes on a hand and then using a glove to hold them in place.

In an embodiment, the method also comprises transmitting EMG signals from the glove to a remote computer or acquisition circuit, for example using a wireless transmitter system or a local memory device.

This disclosed technology, in embodiments, is useful when gripping over time, such as a series of grips participating in a dynamic activity that includes multiple consecutive movements. These movements happen very fast and are originated inside hand muscles. The disclosed technology allows one to find the connection between the activities of muscles and their corresponding hand movements. Then, muscles activity may be played back through their EMG signals that are displayed as distinct patterns.

DETAILED DESCRIPTION OF EMBODIMENTS OF THE DISCLOSED TECHNOLOGY

The disclosed technology described herein provides devices and methods for measuring electromyography (EMG) signals in the hand of a user. This is accomplished by placing a plurality of EMG electrodes/sensors at predetermined locations on a surface of a hand. Then electrodes are connected to wires with snapping connectors. The glove body is then placed on the hand of the user and holds electrodes in place. Each of said EMG electrodes senses a magnitude of an EMG signal over time. Once electrodes are connected to wires, EMG signals are received from the electrodes by a processing circuit, and the processing circuit generates an output proportional to a magnitude of the EMG signals received by the circuit. The electrodes/sensors can be attached to skin separately (gel sensors/electrodes), or they can be embedded in a glove (dry sensors). The output may be presented to the user, for example as a visual representation presented on display located on an external surface of the glove and/or as an audible representation emitted by one or more speakers located on an external surface of the glove. A user has to record the EMG signals from both hands (if both hands are participating in the activity), because the activity of muscles on both hands are important. This can be done separately or in the same time. Then, EMG signals from both hands have to be aligned.

Embodiments of the disclosed technology are described below, with reference to the figures provided.

Figure 1A:
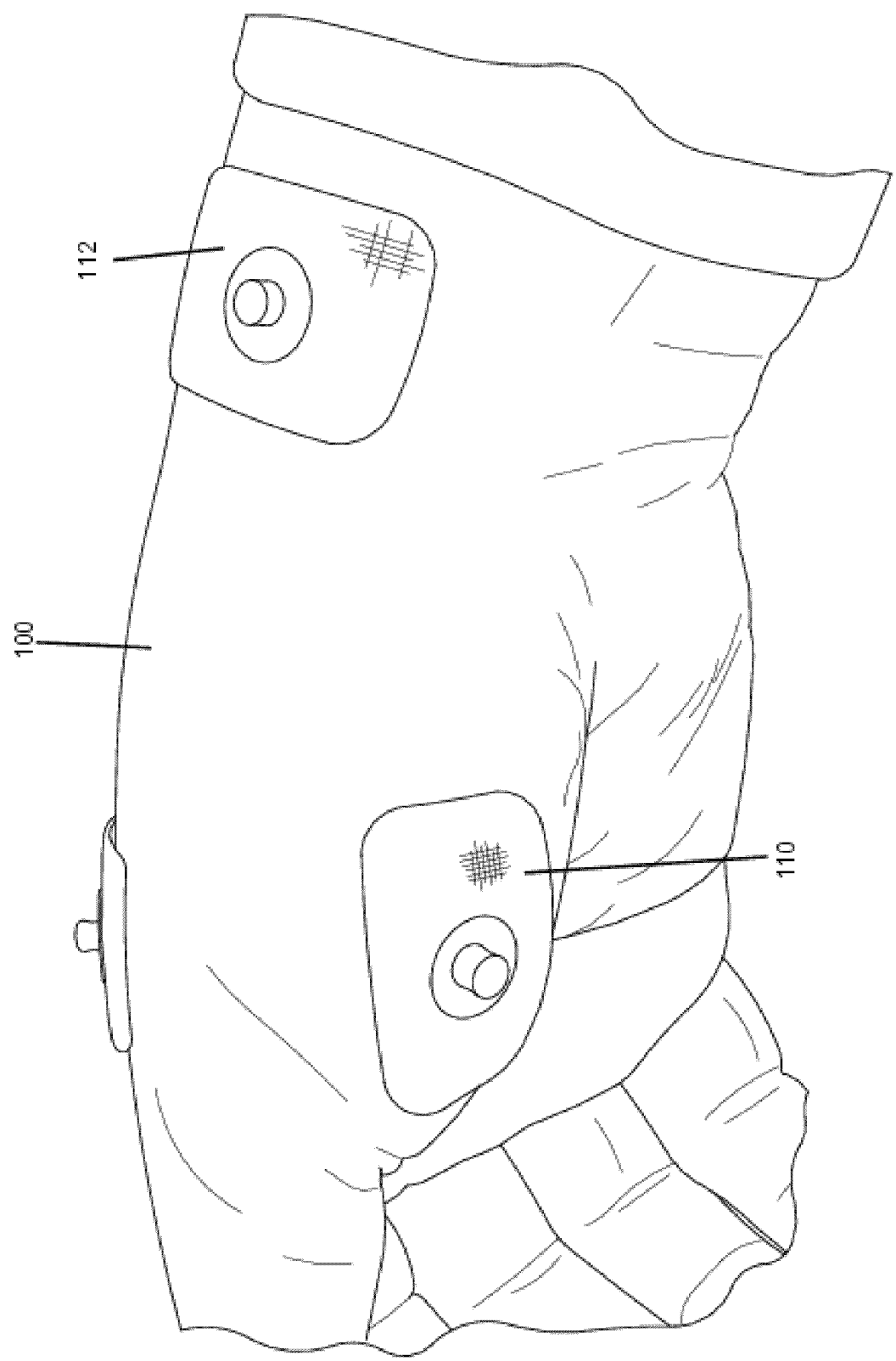
FIGS. 1A, 1B, and 1C, show the placement of EMG electrodes on a user's hand, in an embodiment of the disclosed technology.
Figure 1B:
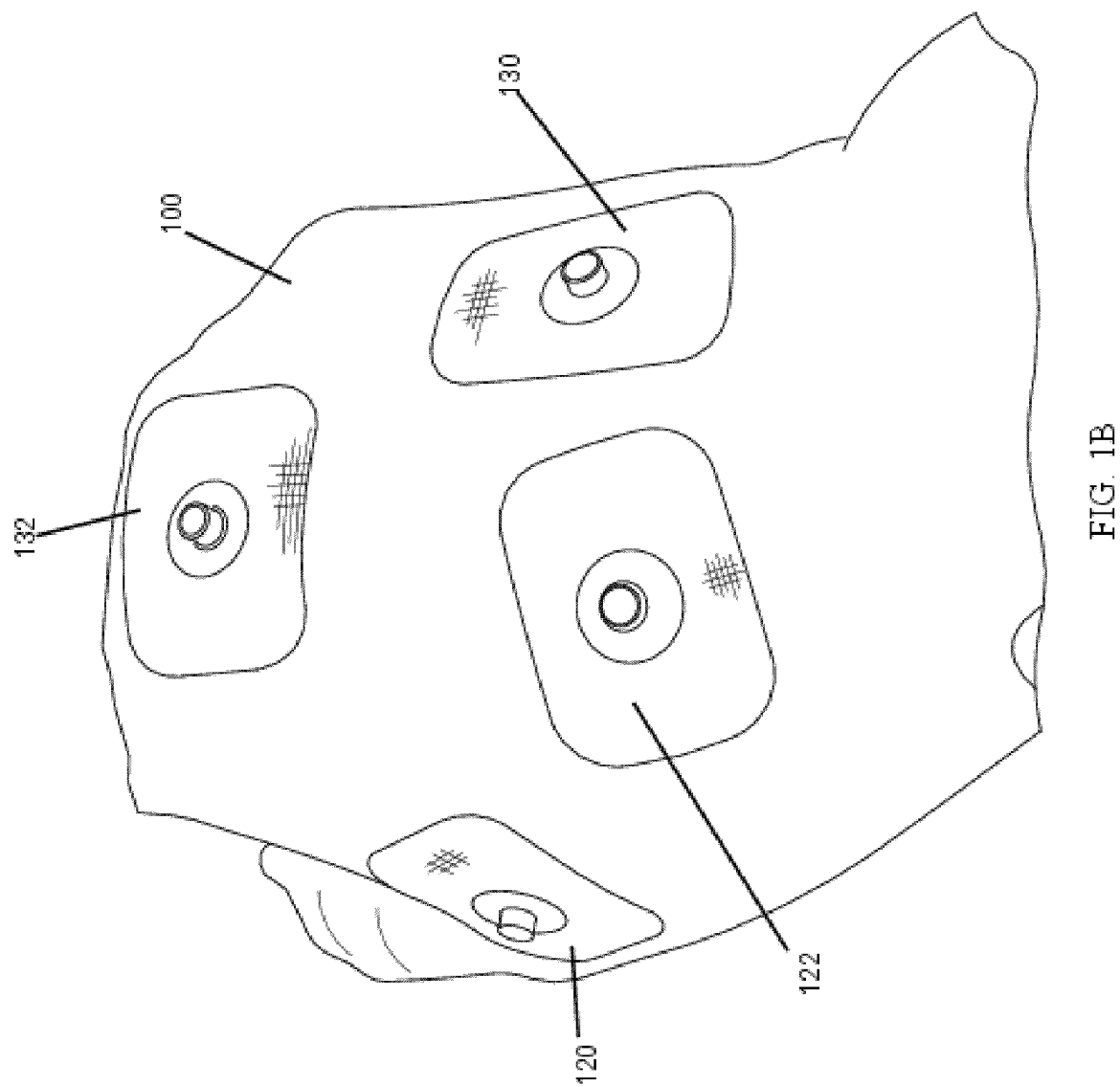
Figure 1C:
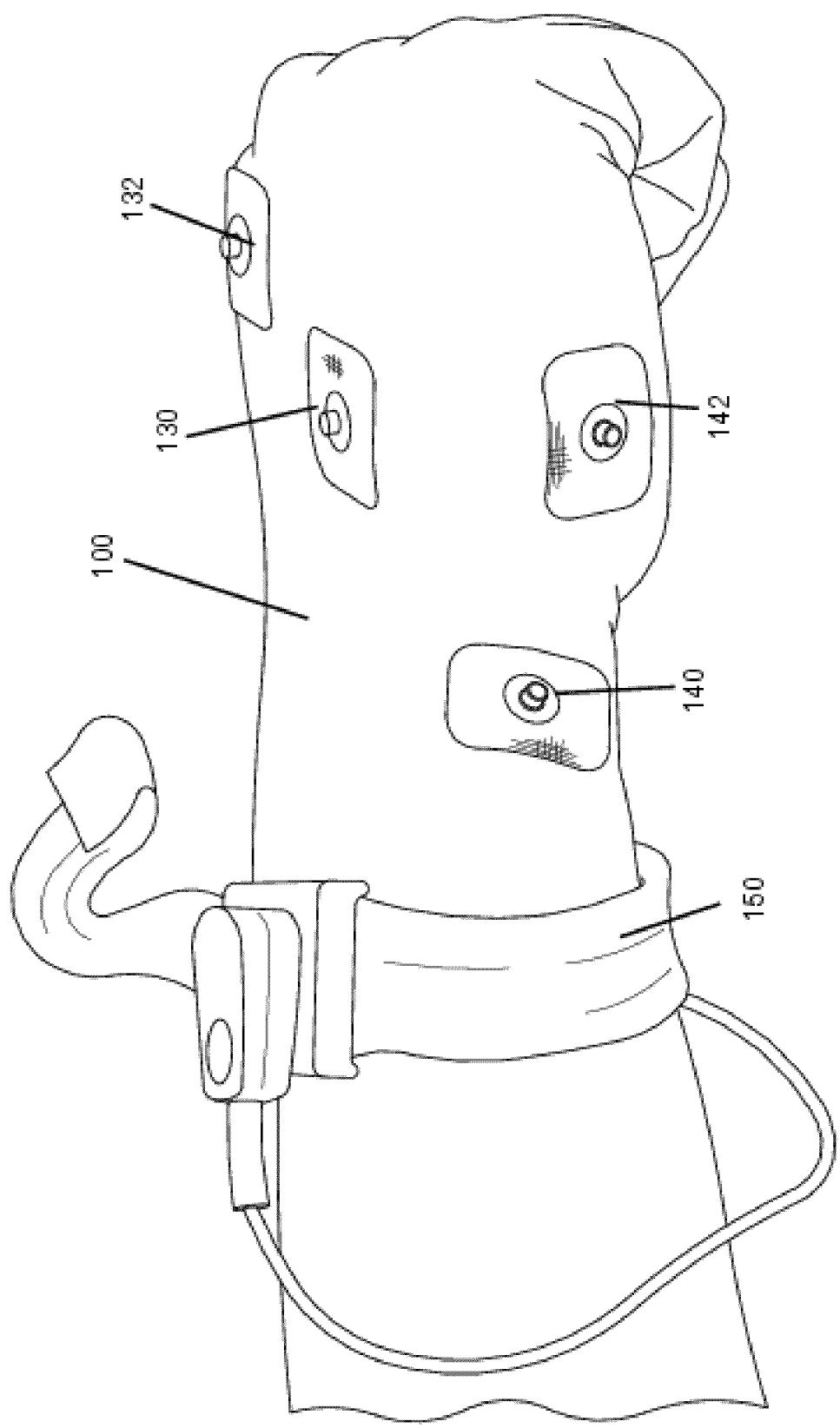

FIGS. 1A, 1B, and 1C, show the placement of EMG electrodes on a user's hand, in an embodiment of the disclosed technology. As seen, four pairs of electrodes are placed at specific locations on a user's hand 100. In each pair of electrodes, one electrode which functions as an active electrode is located above a muscle, and another electrode which functions as a reference electrode is located in a proximity of a bone. A first pair of electrodes, clearly seen in FIG. 1A, includes an active electrode 110 placed below the thumb over a muscle group including the Opponens pollicis and Abductor pollicis brevis muscles, and a reference electrode 112 located above the radius bone. A second pair of electrodes, seen in FIG. 1B, includes an active electrode 120 placed over the first dorsal inerosseus muscle, and a reference electrode 122 placed over the dorsum area of the hand. A third pair of electrodes, seen in FIG. 1B, includes an active electrode 132 placed over the second dorsal inerosseus muscle, and a reference electrode 130 placed over the dorsum area of the hand. A forth pair of electrodes, seen in FIG. 1C, includes an active electrode 142 placed over the Abductor digiti minimi brevis muscle, and a reference electrode 140 place over the ulnar bone. The electronics of all of electrodes 110, 112, 120, 122, 130, 132, 140, and 142, are connected to a ground electrode 150, which may be placed, for example, around the user's wrist, as seen in FIG. 1C.

Figure 5:
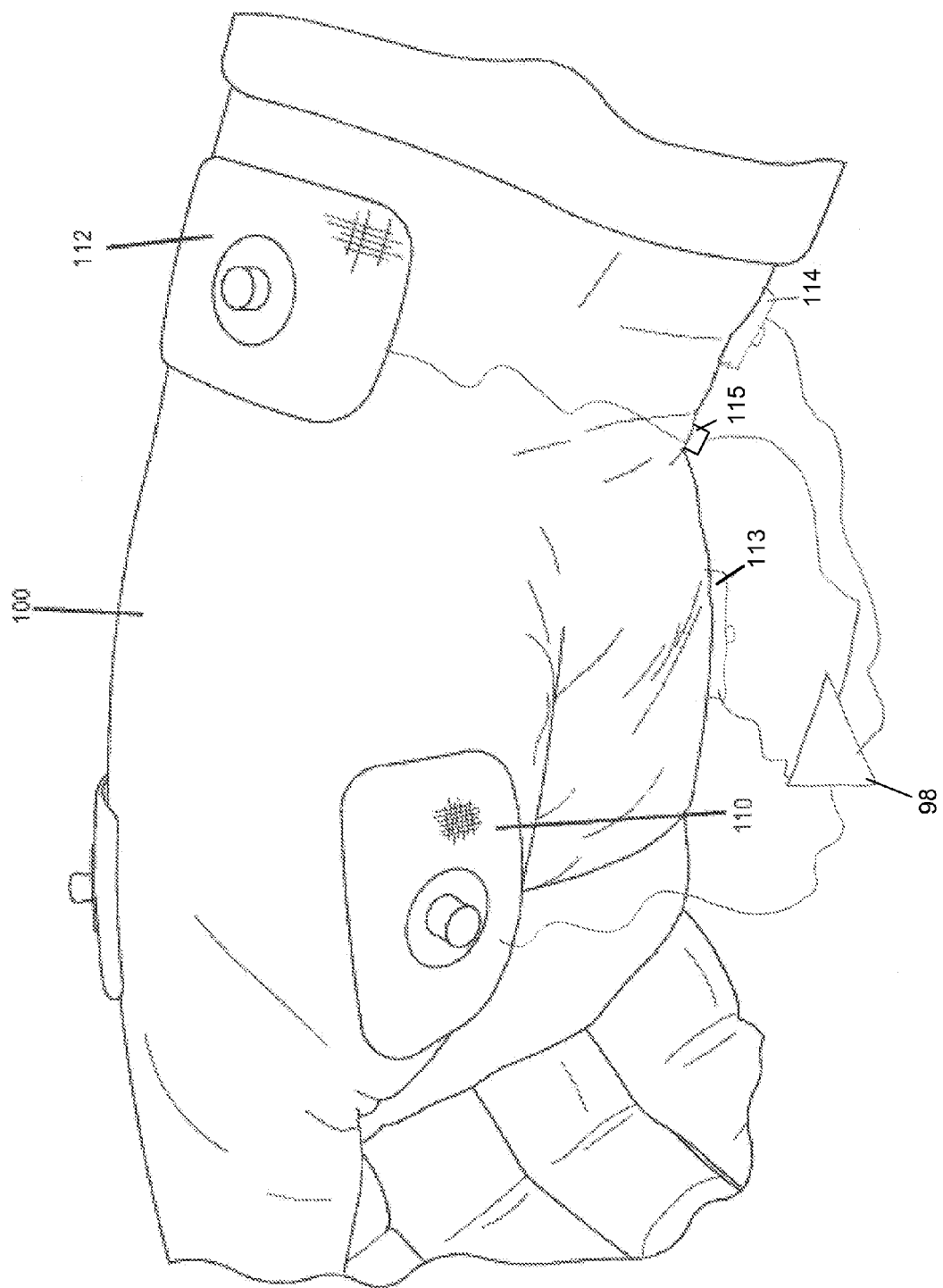
FIG. 5 illustrates a glove comprising two pairs of EMG electrodes, each pair coupled to two inputs of a single differential amplifier.

In an embodiment of the disclosed technology, referring to FIG. 5, each pair of electrodes 110, 113, 114, 115 is electrically coupled to two inputs of a differential amplifier 98. This structure is advantageous for several reasons. First, only one of the channels entering the differential amplifier introduces measurement error, and thus the measurement resulting from the differential amplifier is more accurate. Additionally, differential amplifiers of the type used with the disclosed technology have a high Common Mode Rejection Ratio (CMRR). In differential amplifiers, the CMRR determines the attenuation applied to offset voltage or noise. As is well known, biological signals may have a lot of electrical interference (noise). However, when using a differential amplifier, if both electrodes coupled to the amplifier introduce a relatively high noise, but the voltage difference between the inputs is small, the voltage difference can be measured in a low input range, resulting in high resolution. Furthermore, in order to use EMG signals of the hand for the disclosed technology, the signals must be highly amplified, for example by a factor of 100-1000 or more.

Any suitable EMG electrodes may be used with the disclosed technology. Locations of all electrodes are easily identified on a hand. That said, dry plastic EMG electrodes, not yet commercially available, are advantageous over the typically used gel electrodes because they can be embedded in a glove and can be used immediately. Dry electrodes which may be used in implementing the disclosed technology are described in detail in the applicant's patent application publication numbers 2010/0106044 and 2007/0140562, which are incorporated by reference as if fully set forth herein. In an embodiment, a dry electrode includes a skin contact disk which is implemented as a narrow flexible structure, having a thickness as narrow as 1 mm. In an embodiment, a dry electrode comprises a framework formed of a bulk material of medically approved polysiloxane, and may also comprise conductive nano-particles and/or general purpose electrolyte particles. The electrical conductivity and electrode-to-skin impedance of the electrode disk can be modified by suitably adjusting the ratio of conductive nano-particles to bulk material in the fabricated electrode. It is appreciated that any suitable type of electrodes may be used to implement the disclosed technology, including grid electrodes wherein a number of wires come from a single area of the hand.

Figure 2:
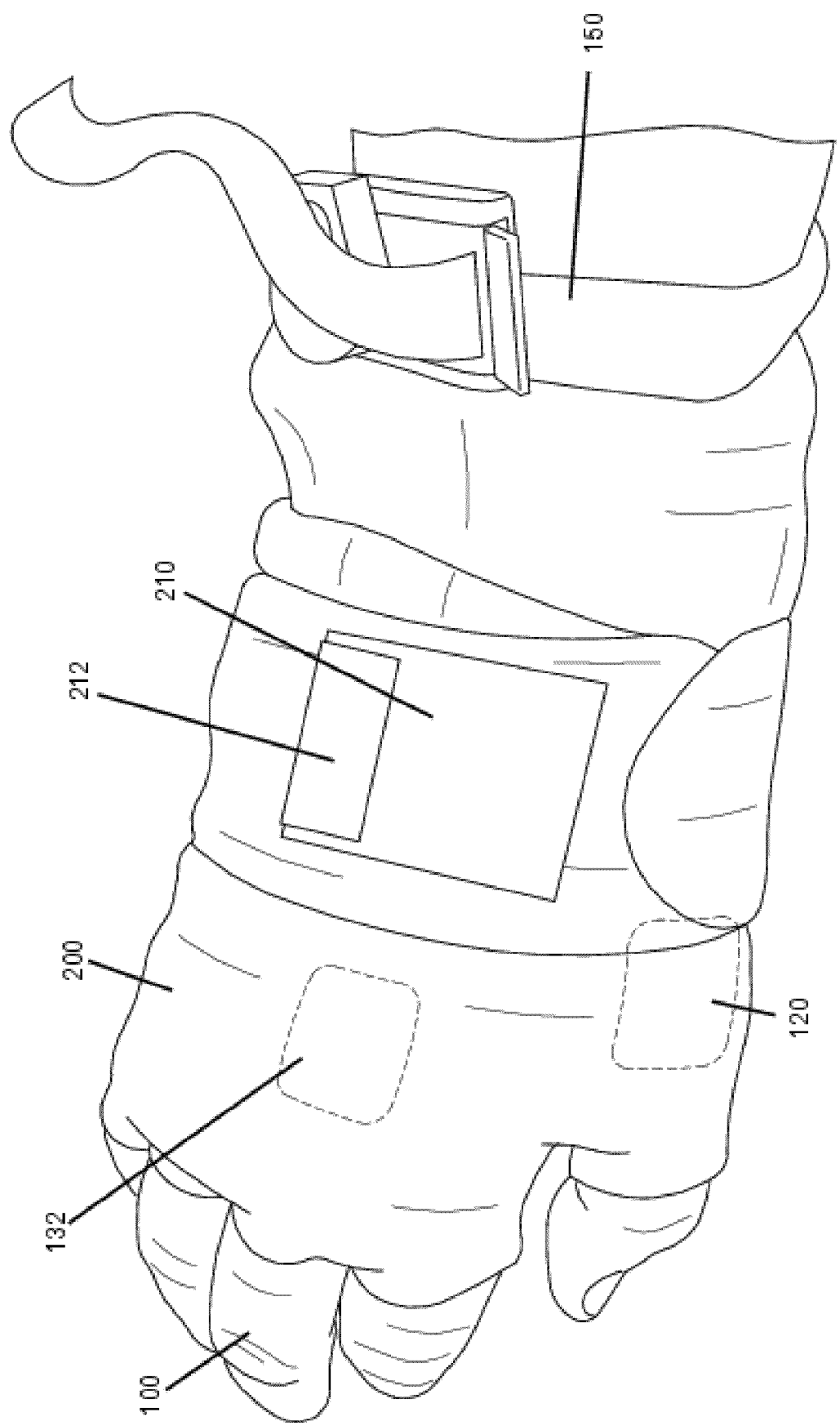
FIG. 2 shows a glove including the electrodes shown in FIGS. 1A, 1B, and 1C, in an embodiment of the disclosed technology.

FIG. 2 shows a glove 200 disposed over the EMG electrodes shown in FIGS. 1A, 1B, and 1C, in an embodiment of the disclosed technology. As seen, the EMG electrodes located under glove 200 are indicated by a dashed line. In the illustrated angle, electrodes 120 and 132 are indicated beneath the glove. In some embodiments, on an external surface of glove 200 are located a display 210 and/or a speaker 212, which are used to provide visual and/or audible feedback to a wearer of the glove as including a representation of the magnitude of the signals measured by the electrodes, as described in further detail with reference to FIGS. 4A and 4B. Additionally, as will be described in further detail herein below, the display 210 and/or speaker 212 may provide to the user a grade or a rating for the dynamic muscle activities applied when gripping an object, such as a golf club, baseball bat, or tennis racket, etc thus helping users improve their grip and reach optimal grip dynamics on the object being held. Different players may have different number of bursts in their EMG signals and they will correspond to their correspondent hand movements, which will be easily identifiable.

In an embodiment, the glove 200 is an existing glove, such as gloves typically used by golf players, which is retrofitted to include EMG electrodes and feedback elements as described herein. Any suitable method of connecting the electrodes to the glove may be used. In some such embodiments, the electrodes may be adhered to an inner surface of the glove, for example using a suitable bonding material such as electrically conductive glue. In another embodiment, the electrodes may be stitched to an inner surface of glove 200. In other embodiments electrodes can be attached to a skin separately from a glove and a glove will hold them in place. In some embodiments, the electrodes may be integrated into the glove material as described in detail herein below, thereby forming an intelligent cloth for EMG recording.

Figure 3A:
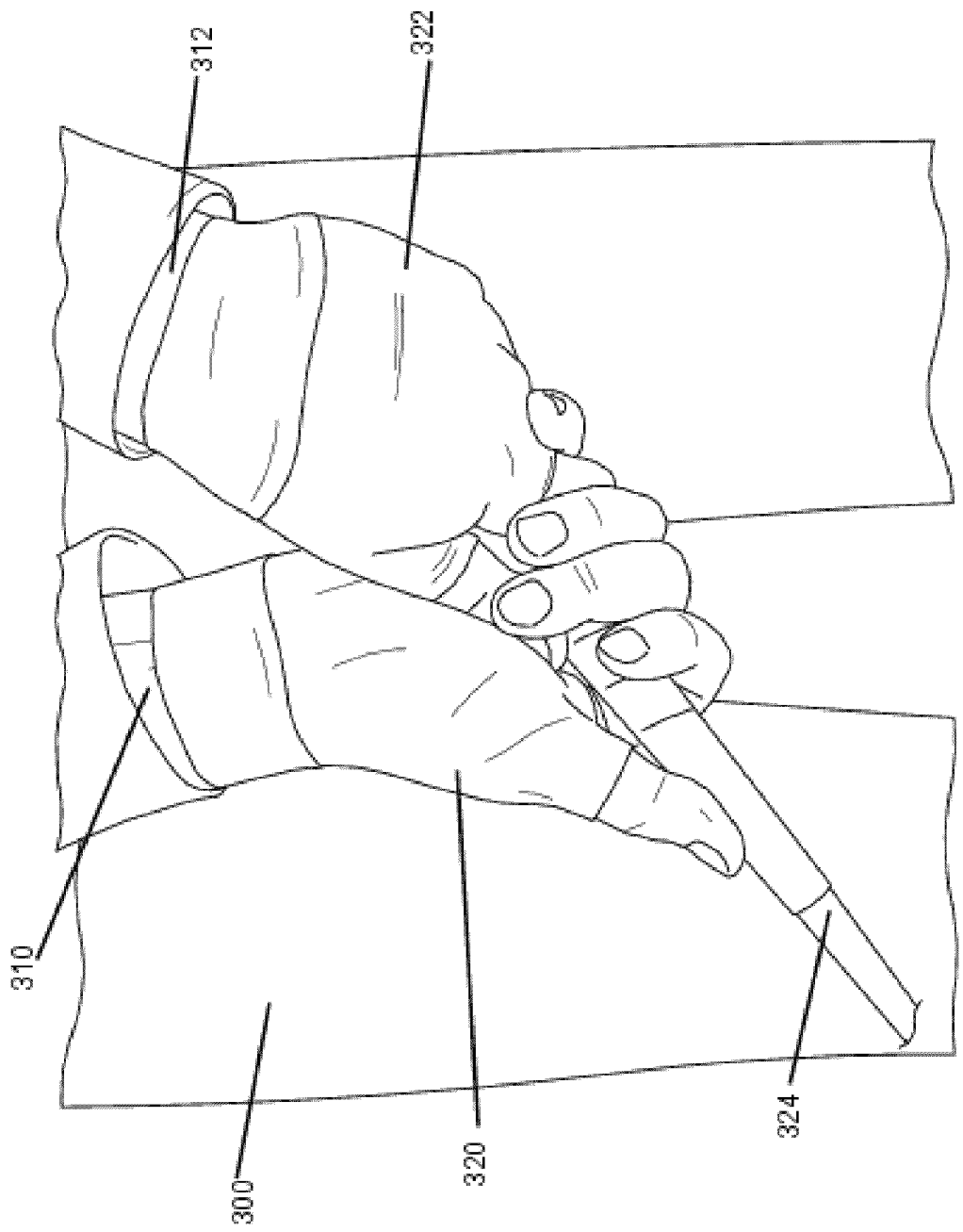
FIGS. 3A, 3B, 3C, and 3D, show four different positions during a golf swing, wherein the dynamic muscle activities in these positions is identified by the electrodes and glove of FIGS. 1A, 1B, 1C, and 2.
Figure 3B:
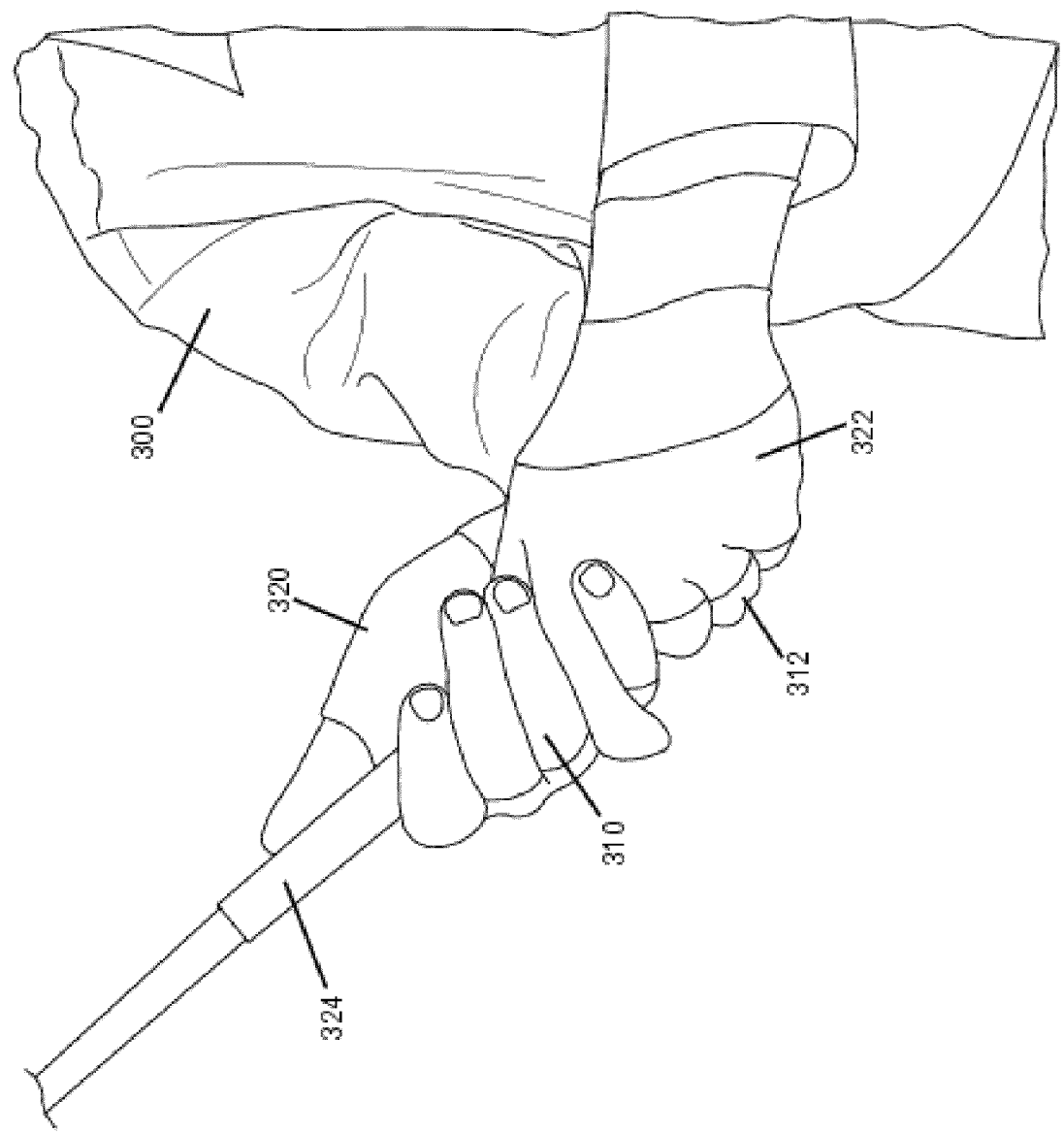
Figure 3C:
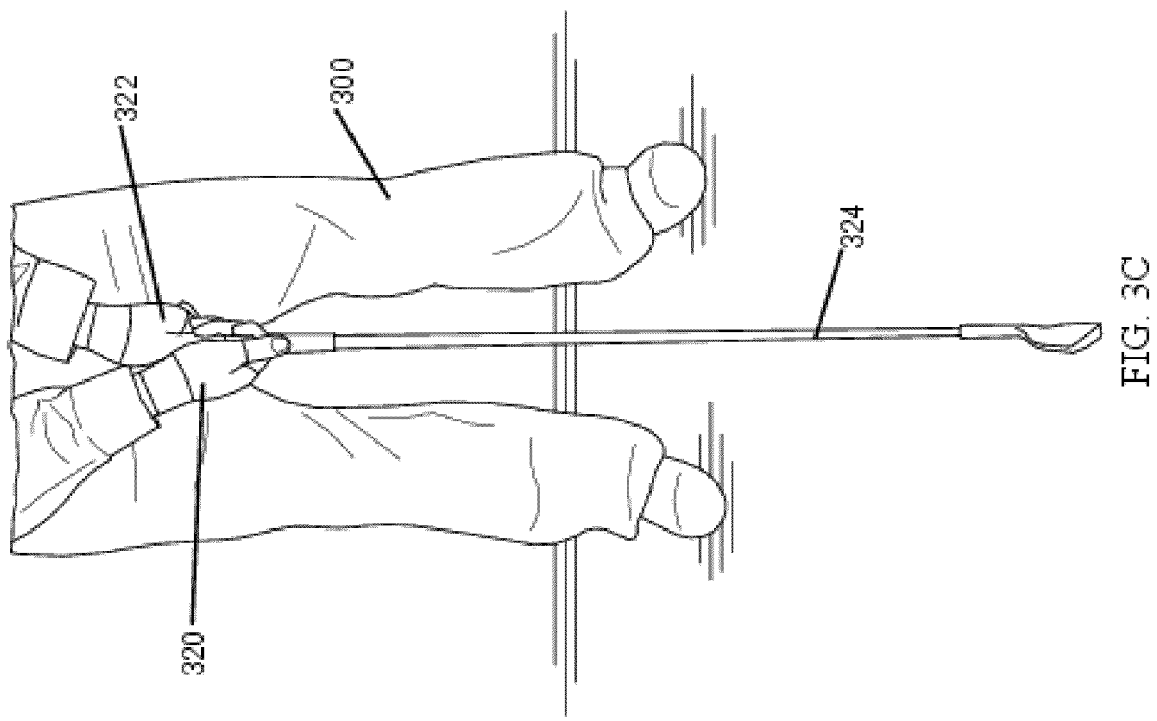
Figure 3D:
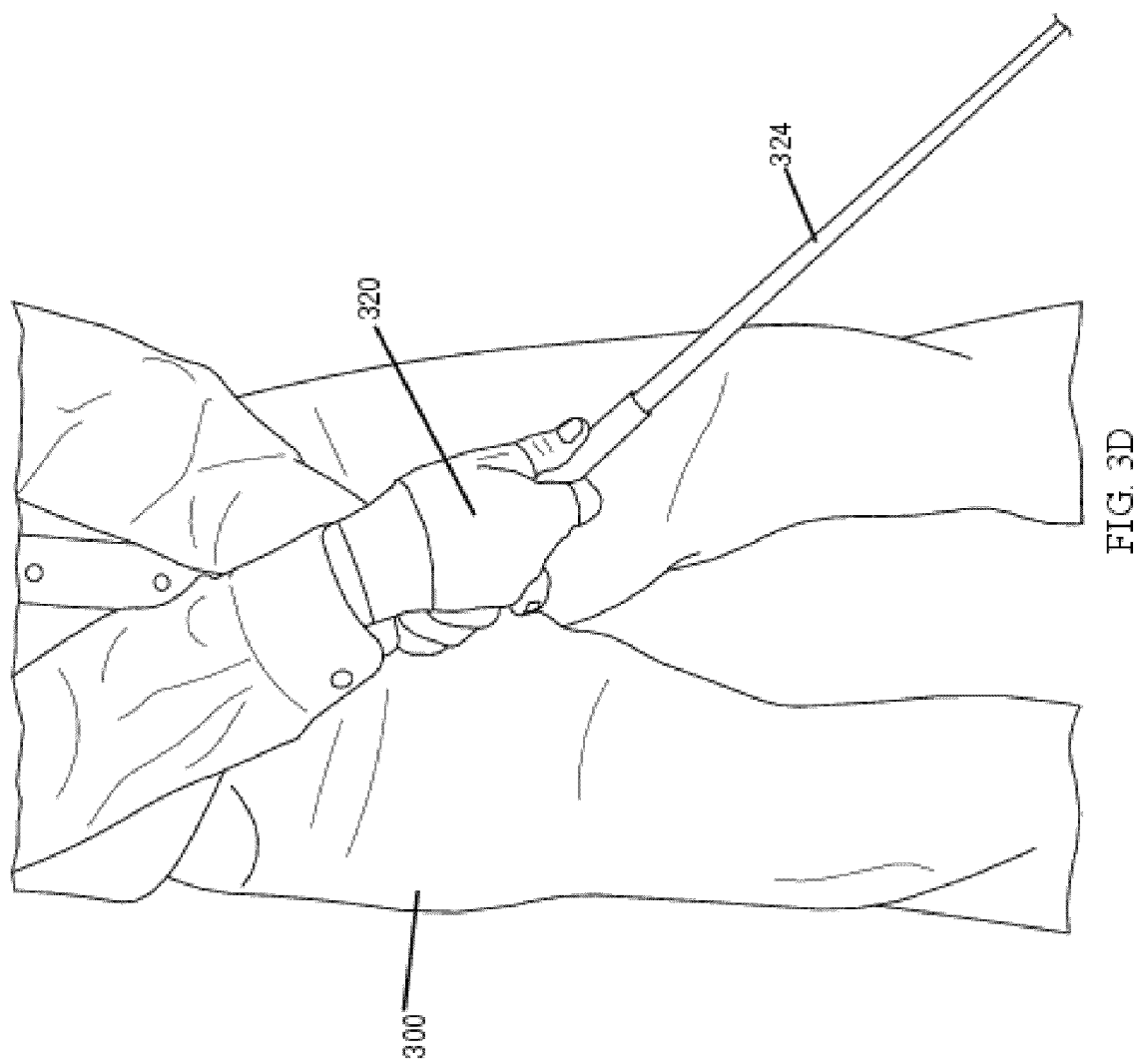

FIGS. 3A, 3B, 3C, and 3D, show four different positions during a golf swing, wherein the dynamic muscle activities in these positions is identified by the electrodes and glove described hereinabove. A user 300 holding a golf club 324 while wearing a right glove 320 of the disclosed technology on his right hand 310 and a left glove 322 of the disclosed technology on his left hand 312. In FIG. 3A, the user 300 is starting to swing the golf club upwards, to build up thrust. In FIG. 3B, the user 300 begins to swing the golf club down toward the ball. In FIG. 3C, the golf club 324 hits the ball (not shown), and in FIG. 3D, the user 300 turns the golf club 324 after hitting the ball.

Figure 4A:
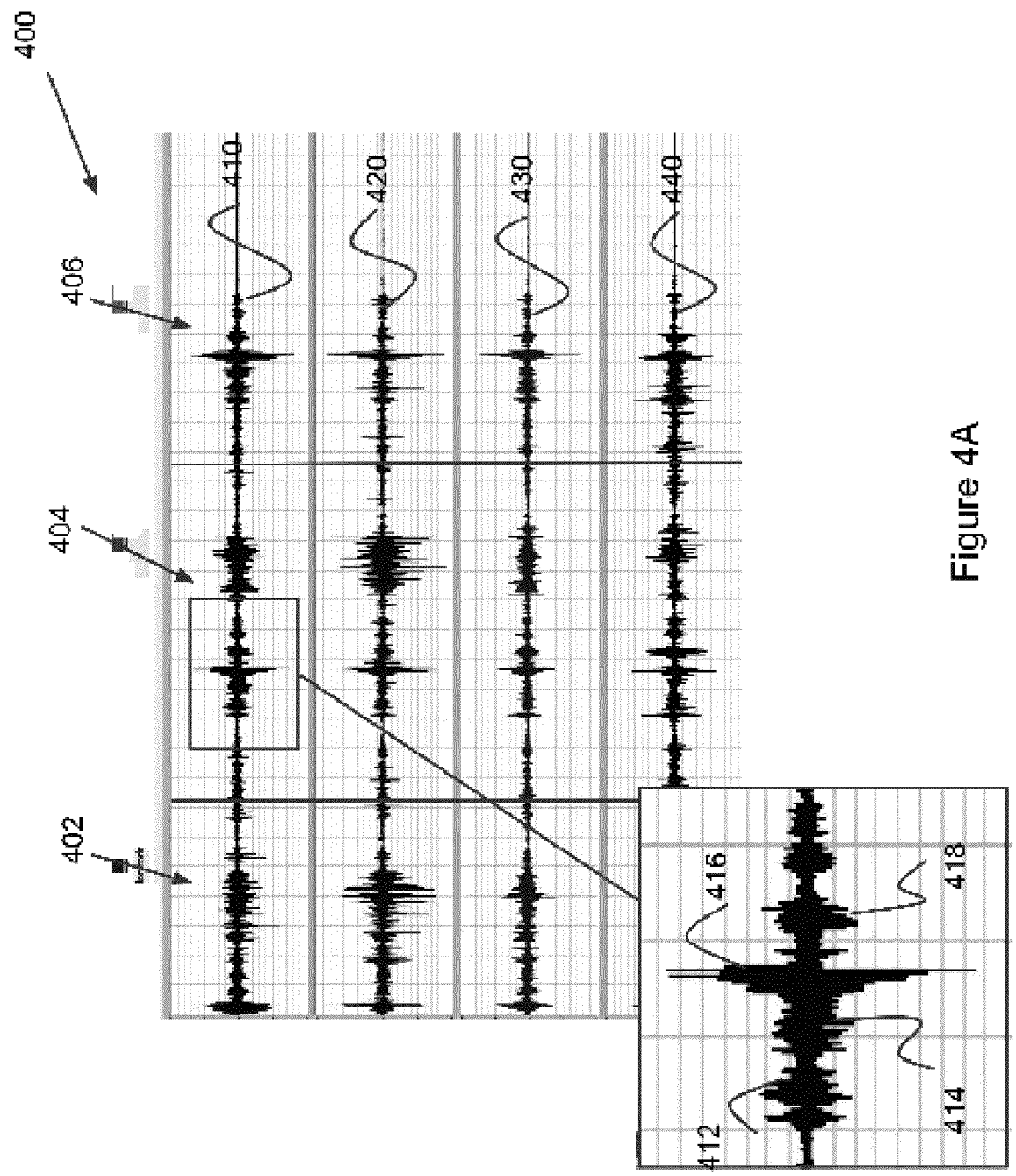
FIGS. 4A (right hand) and 4B (left hand) show an exemplary display of the readings of the electrodes of FIGS. 1A, 1B, and 1C, indicating the positions of FIGS. 3A, 3B, 3C, and 3D.
Figure 4B:
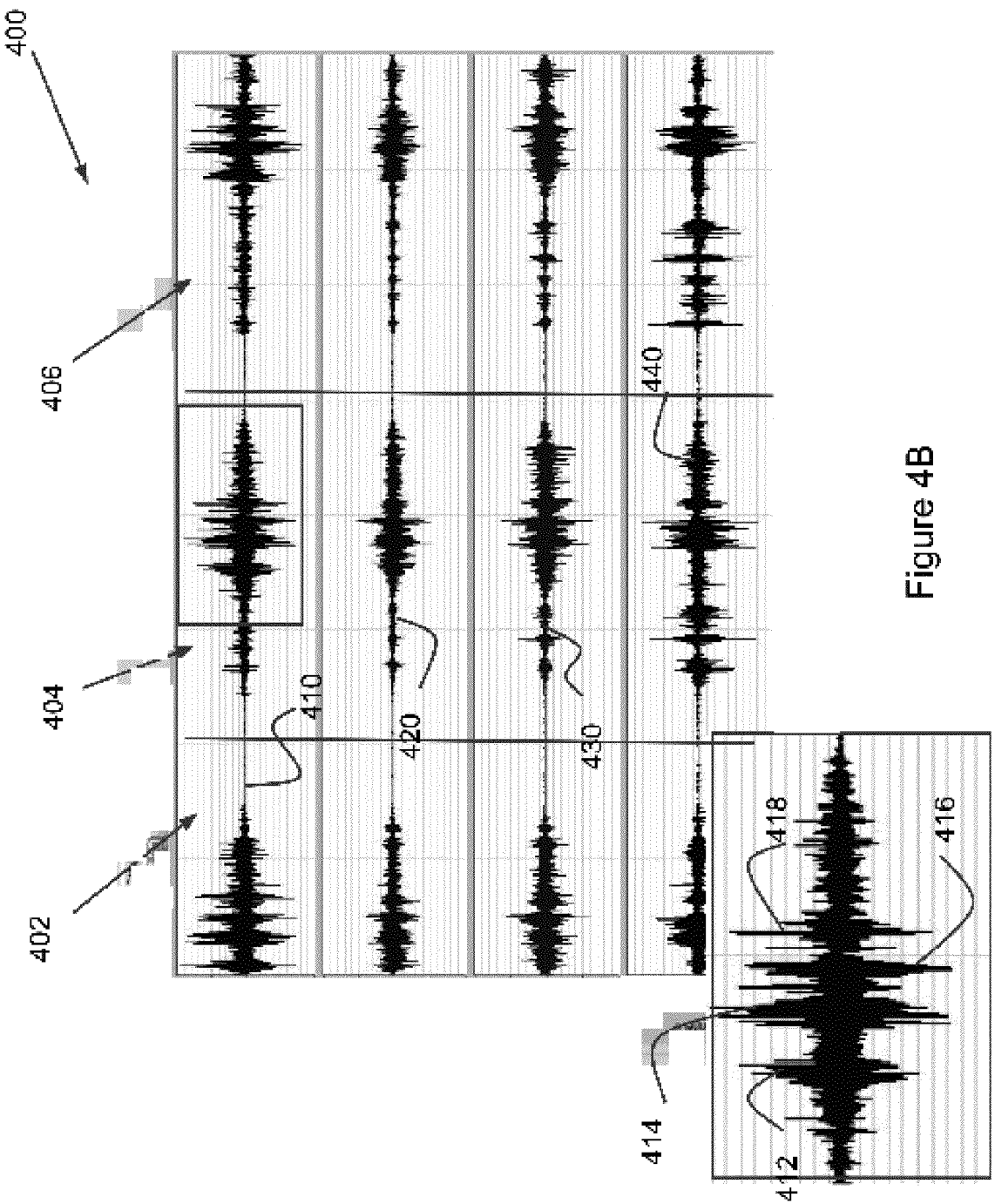

FIGS. 4A and 4B show an exemplary display 400 of the readings of the electrodes of FIGS. 1A, 1B, and 1C, indicating the positions of FIGS. 3A, 3B, 3C, and 3D. FIG. 4A illustrates the signals sensed by electrodes in a glove placed on a user's right hand, and FIG. 4B illustrates the signals sensed by electrodes in a glove on the user's left hand. The four plots 410, 420, 430, and 440 correspond to electrode pairs 110 and 112, 120 and 122, 132 and 130, and 142 and 140, respectively. Additionally, FIGS. 4A (right hand) and 4B (left hand) are divided into three zones, indicated by reference numerals 402, 404, and 406, each zone corresponding to the electrode readings during one golf swing, each swing including the stages shown in FIGS. 3A to 3D. For clarity purposes, the following description relates only to the portion of plot 410 appearing in the central zone 404, though it is appreciated that the same discussion is equally applicable to the portions of all the plots appearing in other zones.

As seen, plot 410 includes four bursts or peaks, indicated by reference numerals 412, 414, 416, and 418. Each of the bursts corresponds to one of the positions shown in FIGS. 3A to 3D, such that burst 412 corresponds to the position of FIG. 3A, where the user swings the golf club upward, burst 414 corresponds to the position of FIG. 3B, where the user begins to bring the golf club down, burst 416 corresponds to the position of FIG. 3C, where the user hits the ball, and burst 418 corresponds to the position of FIG. 3D, where the golf club swings back after hitting the ball.

As clearly seen in FIGS. 4A and 4B, spike 416 is taller than the surrounding bursts, indicating that the muscles apply the strongest grip to the golf club when the ball is being hit. This type of signal structure corresponds to the optimal grip of a golf club during a swing. In contrast, the signals received from electrodes placed on the hands of bad players show high peaks, indicating strong grip of the club, in at least two of the positions of FIGS. 3A to 3D, and sometimes in all four positions. Thus, a golfer looking at a plot such as plot 410 on display 210 of his glove may identify the number of tall peaks in his swing, and conclude when his grip must be loosened in order to improve his swing.

Additionally, comparison of FIGS. 4A and 4B, shows that in FIG. 4A which represents the electrode readings on the user's right hand, the spike 416 is taller than the corresponding spike 416 in FIG. 4B. Thus, one can conclude that the user is a right handed golfer, and that the right hand applies more force to the golf club during the swing and hit. If a golfer sees on displays 210 that the plots for both hands show spikes of the same magnitude, he can conclude that his weaker hand is applying too much force to the golf club, and that the weaker hand should loosen its grip in order to improve the swing.

It is appreciated that though the illustrated embodiments of FIGS. 3A to 3D and 4A and 4B demonstrate the disclosed technology with respect to a golf player and the muscle activity or dynamic strength of grip applied to a golf club, the disclosed technologies can equally be applied to a tennis player gripping a tennis racket, a baseball player gripping a baseball bat, and any other situation in which a user has to grip an object at an optimal strength. It is further appreciated that the glove and electrodes of the disclosed technology are sensitive to dynamic forces translated in EMG signals of muscles applied to the shaft or golf club from any direction, including forces that are off-axis to the measuring surface, and not just to forces applied perpendicular to the electrode measuring surface.

As described hereinabove, the EMG electrodes may be attached to the glove 200 in any suitable way, including separately attached to a skin electrodes, adhering the electrodes to the glove, sewing the electrodes into the glove, and integrating the electrodes in the fabric of the glove.

Gel EMG electrodes such as electrodes 110 and 112 are shown on FIG. 1A. Dry EMG electrodes may consist of more than one components, and all the electrode components are integrated in the material of glove 200, typically using suitable glue on a laywer of PDMS (Polydimethylsiloxane). The process of integrating the electrode in the material of glove 200 may, in some embodiments, include multiple steps. Initially, dry EMG electrodes in the form of disks or other suitable shapes, and a flexible Printed Circuit Board (PCB) are provided. The electrode disks and flexible PCB are connected to one another with a layer of suitable conductive glue, not yet commercially available, which glue is then tempered until it is sufficiently dry. A layer of a suitable textile adhesive, not yet commercially available is used to connect the flexible PCB to the textile of the glove 200, and the adhesive is tempered until it is sufficiently dry. A signal wire is soldered to the flexible PCB at a soldering point, for transfer of the signals sensed by electrodes to a suitable processor (not shown) or for presentation on display 210 of glove 200. In some embodiments, a standard ECG press stud (not shown), not yet commercially available, is soldered onto the flexible PCB. The soldering point is then encapsulated with a silicone layer, which is subsequently tempered. As a result, an intelligent fabric for sensing EMG signals is formed.

Figure 6:
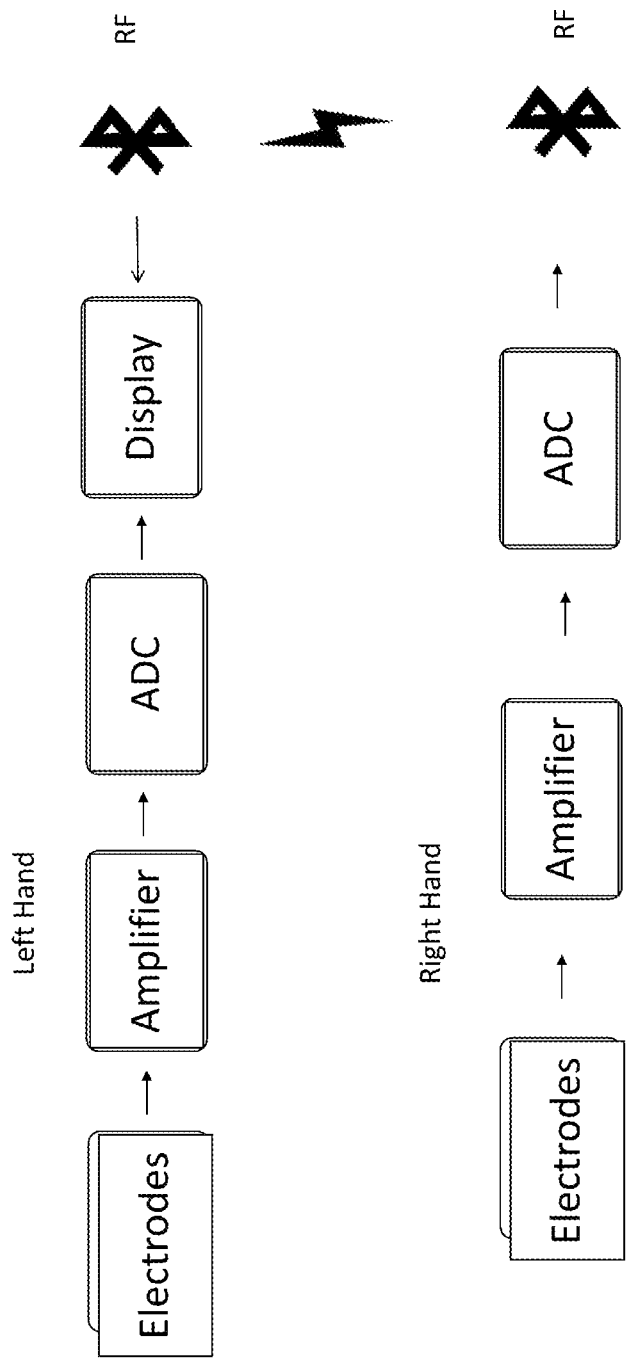
FIG. 6 shows a high-level block diagram of a circuit that may be used in a data acquisition system receiving signals from electrodes carrying out the disclosed technology.

FIG. 6 shows a high-level block diagram of a circuit that may be used in a data acquisition system receiving signals from electrodes carrying out the disclosed technology. An instrumentation amplifier is associated with each electrode pair, and is used to prevent the interference from other devices. A programmable filter, associated with each electrode pair, includes an anti-aliasing component. EGLOO Nano is a very small size field programmable gate array (FPGA) without external memory. FPGA is a configurable integrated circuit. Data acquisition system (DAS) includes a programmable gain amplifier (PGA), a sample & hold (S&H) device, an analog multiplexor (AMUX), an analog-to-digital converter (ADC), and a dissemination filter. The S&H device helps a condensator to hold a voltage during digitizing. The circuit includes a low noise drop out regulator (LDO) and direct current converter (DC converter). In some embodiments, circuit 600 includes an RF interface, which may be used to collect data from the data acquisition system in a central monitoring computer, for example as described herein below with reference to FIG. 7.

Figure 7:
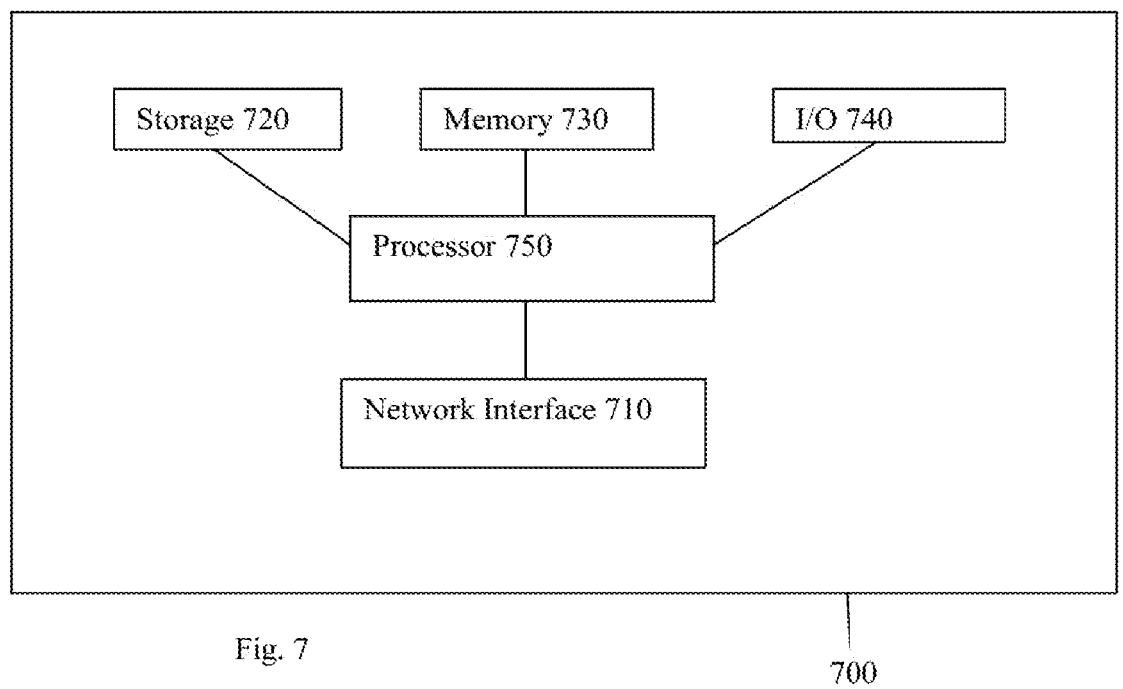
FIG. 7 shows a high-level block diagram of a device that may be used to carry out the disclosed technology.

FIG. 7 shows a high-level block diagram of a device that may be used to carry out the disclosed technology. Device 700 comprises a processor 750 that controls the overall operation of the computer by executing the device's program instructions which define such operation. The device's program instructions may be stored in a storage device 720 (e.g., magnetic disk, database) and loaded into memory 730 when execution of the console's program instructions is desired. Thus, the device's operation will be defined by the device's program instructions stored in memory 730 and/or storage 720, and the console will be controlled by processor 750 executing the console's program instructions. A device 700 also includes one or a plurality of input network interfaces for communicating with other devices, such as an electronic circuit of a glove 200, via a network (e.g., the internet). The device 700 further includes an electrical input interface. A device 700 also includes one or more output network interfaces 710 for communicating with other devices, such as glove 200. Specifically, in some embodiments device 700 includes an RF interface (not shown) for communication with RF interface 650 of FIG. 6. Device 700 also includes input/output 740 representing devices which allow for user interaction with a computer (e.g., display, keyboard, mouse, speakers, buttons, etc.). One skilled in the art will recognize that an implementation of an actual device will contain other components as well, and that FIG. 7 is a high level representation of some of the components of such a device for illustrative purposes. It should also be understood by one skilled in the art that the method and devices depicted in FIGS. 1 through 6 may be implemented in a glove configured to communicate with a device such as is shown in FIG. 7.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods, systems, and devices described herein-above are also contemplated and within the scope of the disclosed technology.

I claim:

1. A glove for measuring electromyography (EMG) signals in a hand comprising:
   a glove body;
   a plurality of EMG electrodes disposed at predetermined locations on an inner surface of said glove body and configured to sense a magnitude of a plurality of EMG signals over a period of time, wherein said EMG electrodes are disposed at locations targeted to specific muscle locations on a hand of a user when said glove body is worn;

a data acquisition circuit coupled to said plurality of EMG electrodes and configured to receive at least one of said plurality of EMG signals and to generate an output proportional to said magnitude of said at least one of said plurality of EMG signals sensed by at least one of said plurality of EMG electrodes; and a user feedback module located on an external surface of said glove body and configured to provide a representation of said output of said data acquisition circuit, wherein said plurality of EMG electrodes comprises at least two pairs of EMG electrodes, each pair coupled to two inputs of a single differential amplifier, such that a first EMG electrode of one of said pairs of EMG electrodes is electrically coupled to said single differential amplifier and comprises an active electrode and senses EMG signals from a muscle of the hand, and a second EMG electrode of said pair of EMG electrodes is coupled to said single differential amplifier and comprises a reference electrode which senses EMG signals from an area of a bone of the hand.

2. The glove of claim 1, wherein, when said glove body is worn by a user, said first EMG electrode senses EMG signals from the Opponens pollicis muscle and the Abductor pollicis brevis muscle and said second EMG electrode senses EMG signals from an area of the radius bone.

3. The glove of claim 1, wherein when said glove body is worn by a user, said first EMG electrode senses EMG signals from the First dorsal interosseus muscle and the second EMG electrode senses EMG signals from a Dorsum section of the hand.

4. The glove of claim 1, wherein when said glove body is worn by a user, said first EMG electrode senses EMG signals from the Second dorsal interosseus muscle and the second EMG electrode senses EMG signals from a Dorsum section of the hand.

5. The glove of claim 1, wherein when said glove body is worn by a user, said first EMG electrode senses EMG signals from the Abductor digiti minimi brevis muscle and the second EMG electrode senses EMG signals from an area of the Ulnar bone.

6. A method for measuring electromyography (EMG) signals in the hand comprising:

placing a plurality of EMG electrodes on a hand of a user, such that said EMG electrodes are disposed at specific muscle locations on said hand and each of said EMG electrodes senses a magnitude of an EMG signal over time, said plurality of EMG electrodes including at least two pairs of EMG electrodes such that a first EMG electrode of one of said two pairs of EMG electrodes is placed such that EMG signals are received from a muscle of the hand and a second EMG electrode of said one of said two pairs is placed above a bone of the hand to sense EMG signals from an area of the bone of the hand, wherein said first electrode functions as an active electrode and said second electrode functions as a reference electrode;

coupling each said pair of EMG electrodes to two inputs of a single differential amplifier;

receiving at least one EMG signal from at least one of said plurality of EMG electrodes;

generating an output proportional to a magnitude of said received at least one EMG signal; and providing a representation of said output to said user.

7. The method of claim 6, wherein said placing a plurality of EMG electrodes comprises placing said first EMG electrode above the Opponens pollicis muscle and the Abductor pollicis brevis muscle and placing said second EMG electrode above the radius bone.

8. The method of claim 6, wherein said placing a plurality of EMG electrodes comprises placing the first EMG electrode above the First dorsal interosseus muscle and placing the second EMG electrode above a Dorsum area of the hand.

9. The method of claim 6, wherein said placing a plurality of EMG electrodes comprises placing said first EMG electrode above the Second dorsal interosseus muscle and placing the second EMG electrode above a Dorsum area of the hand.

10. The method of claim 6, wherein said placing a plurality of EMG electrodes comprises placing said first EMG electrode above the Abductor digiti minimi brevis muscle and placing the second EMG electrode above the Ulnar bone.

11. The method of claim 6, wherein said receiving further comprises receiving EMG signals from at least one of said plurality of EMG electrodes at at least two time points during a golf swing, and wherein said providing a representation comprises providing to said user a representation of the pressure applied to a golf club held by said hand at said at least two time points during said golf swing, said at least two time points during said golf swing including time points during at least two of the following actions:

raising of the golf club;
lowering the golf club towards the ball;
hitting the ball; and
swinging said golf club after hitting said ball.

12. An electromyography (EMG) signal measuring system, comprising:

a plurality of EMG electrodes disposed at predetermined locations on a glove, said EMG electrodes configured to sense a magnitude of a plurality of EMG signals over a period of time, wherein said EMG electrodes are disposed at locations targeted to specific muscle locations on a hand of a user when said glove is worn by said user;

a data acquisition circuit coupled to said plurality of EMG electrodes, configured to receive at least one of said plurality of EMG signals and to generate an output proportional to said magnitude of said at least one of said plurality of EMG signals sensed by at least one of said plurality of EMG electrodes; and a user feedback electrically coupled to said data acquisition circuit;

wherein said predetermined locations on said hand comprise at least two of the following pairs:

a) above the Opponens pollicis muscle and the Abductor pollicis brevis muscle; and above the radius bone;
b) above the First dorsal interosseus muscle; and above a Dorsum area of said hand;
c) above the Second dorsal interosseus muscle; and above the Dorsum area of said hand;
d) above the Abductor digiti minimi brevis muscle; and above the Ulnar bone;

wherein at least two pairs of said EMG electrodes is coupled to two inputs of a single differential amplifier, such that a first EMG electrode of one of said pairs of EMG electrodes is electrically coupled to said single differential amplifier and comprises an active electrode and senses EMG signals from a muscle of the hand, and a second EMG electrode of said pair of EMG electrodes is coupled to said single differential amplifier and comprises a reference electrode which senses EMG signals from an area of a bone of the hand.

* * * * *